(12) United States Patent
Dionne et al.

(10) Patent No.: US 7,207,982 B2
(45) Date of Patent: Apr. 24, 2007

(54) OSMOTIC PUMP WITH MEANS FOR DISSIPATING INTERNAL PRESSURE

(75) Inventors: Keith E. Dionne, Cambridge, MA (US); Robert Mosbauer, San Francisco, CA (US); Craig R. Davis, Newark, CA (US); John R. Peery, Stanford, CA (US)

(73) Assignee: Alza Corporation, Mountain View, CA (US)

( * ) Notice: Subject to any disclaimer, the term of this patent is extended or adjusted under 35 U.S.C. 154(b) by 202 days.

(21) Appl. No.: 10/814,801

(22) Filed: Mar. 31, 2004
(Under 37 CFR 1.47)

(65) Prior Publication Data
US 2005/0070884 A1    Mar. 31, 2005

Related U.S. Application Data

(60) Provisional application No. 60/459,296, filed on Mar. 31, 2003.

(51) Int. Cl.
*A61K 9/22* (2006.01)
*A61F 13/00* (2006.01)

(52) U.S. Cl. .................... 604/892.1; 424/422
(58) Field of Classification Search ............ 424/473, 424/422, 423, 438; 604/890.1, 892.1
See application file for complete search history.

(56) References Cited

U.S. PATENT DOCUMENTS

| | | | |
|---|---|---|---|
| 3,797,492 A | 3/1974 | Eckenhoff et al. | |
| 3,987,790 A | 10/1976 | Eckenhoff et al. | |
| 4,008,719 A | 2/1977 | Theeuwes et al. | |
| 4,305,927 A | 12/1981 | Theeuwes et al. | |
| 4,865,845 A | 9/1989 | Eckenhoff et al. | |
| 4,874,388 A | 10/1989 | Wong et al. | |
| 5,034,229 A | 7/1991 | Magruder et al. | |
| 5,057,318 A | 10/1991 | Magruder et al. | |
| 5,059,423 A | 10/1991 | Magruder et al. | |
| 5,110,596 A | 5/1992 | Magruder et al. | |
| 5,112,614 A | 5/1992 | Magruder et al. | |
| 5,137,727 A | 8/1992 | Eckenhoff | |

(Continued)

FOREIGN PATENT DOCUMENTS

WO    WO 98/27962    7/1998

(Continued)

OTHER PUBLICATIONS

International Search Report dated Nov. 4, 2004 (5 pages).

(Continued)

*Primary Examiner*—Sharon E. Kennedy
(74) *Attorney, Agent, or Firm*—TraskBritt

(57) ABSTRACT

The present invention includes an osmotic pump that includes a means for venting an osmotic composition included in the pump before the internal pressure of the pump has the opportunity to build to such an extent that the pump is structurally compromised, such as when one or more components of the pump are physically separated. The means for venting osmotic material included in an osmotic pump according to the present invention includes a vent that allows the material included in the osmotic composition of the pump to dissipate into an environment of operation at a rate that results in dissipation of the pressure created within the osmotic pump and a reduced potential for subject discomfort or irritation.

24 Claims, 1 Drawing Sheet

U.S. PATENT DOCUMENTS

| | | | |
|---|---|---|---|
| 5,151,093 A | 9/1992 | Theeuwes et al. | |
| 5,219,572 A | 6/1993 | Sivaramakrishnan et al. | |
| 5,234,692 A | 8/1993 | Magruder et al. | |
| 5,234,693 A | 8/1993 | Magruder et al. | |
| 5,279,608 A | 1/1994 | Cherif Cheikh | |
| 5,308,348 A | 5/1994 | Balaban et al. | |
| 5,312,389 A * | 5/1994 | Theeuwes et al. | 604/892.1 |
| 5,336,057 A | 8/1994 | Fukuda et al. | |
| 5,368,588 A | 11/1994 | Bettinger | |
| 5,511,355 A | 4/1996 | Dingler | |
| 5,557,318 A | 9/1996 | Gabriel | |
| 5,713,847 A | 2/1998 | Howard, III et al. | |
| 5,728,396 A | 3/1998 | Peery et al. | |
| 5,836,935 A | 11/1998 | Ashton et al. | |
| 5,874,388 A | 2/1999 | Hsu | |
| 5,976,109 A | 11/1999 | Heruth | |
| 5,985,305 A | 11/1999 | Peery et al. | |
| 5,997,527 A | 12/1999 | Gumucio et al. | |
| 5,997,902 A | 12/1999 | Maruyama et al. | |
| 6,113,938 A | 9/2000 | Chen et al. | |
| 6,132,420 A | 10/2000 | Dionne et al. | |
| 6,156,331 A | 12/2000 | Peery et al. | |
| 6,217,906 B1 | 4/2001 | Gumucio et al. | |
| 6,248,112 B1 | 6/2001 | Gambale et al. | |
| 6,261,584 B1 | 7/2001 | Peery et al. | |
| 6,270,787 B1 | 8/2001 | Ayer | |
| 6,283,949 B1 | 9/2001 | Roorda | |
| 6,375,978 B1 | 4/2002 | Kleiner et al. | |
| 6,395,292 B2 | 5/2002 | Peery et al. | |
| 6,436,091 B1 | 8/2002 | Harper et al. | |
| 6,447,522 B2 | 9/2002 | Gambale et al. | |
| 6,468,961 B1 | 10/2002 | Brodbeck et al. | |
| 6,508,808 B1 * | 1/2003 | Carr et al. | 604/892.1 |
| 6,840,931 B2 * | 1/2005 | Peterson et al. | 604/892.1 |
| 2003/0044467 A1 | 3/2003 | Brodbeck et al. | |
| 2003/0059376 A1 | 3/2003 | Libbey, III et al. | |
| 2003/0108609 A1 | 6/2003 | Berry et al. | |
| 2003/0180364 A1 | 9/2003 | Chen et al. | |
| 2003/0215515 A1 | 11/2003 | Truong-le et al. | |
| 2004/0001889 A1 | 1/2004 | Chen et al. | |
| 2004/0024069 A1 | 2/2004 | Chen et al. | |
| 2004/0151753 A1 | 8/2004 | Chen et al. | |
| 2004/0224903 A1 | 11/2004 | Berry et al. | |
| 2005/0095284 A1 * | 5/2005 | Trautman | 424/451 |

FOREIGN PATENT DOCUMENTS

| | | |
|---|---|---|
| WO | WO 99/33446 A | 7/1999 |
| WO | WO 00/45790 | 8/2000 |
| WO | WO 00/54745 A2 | 9/2000 |
| WO | WO 01/43528 A2 | 12/2000 |
| WO | WO 01/51041 A | 7/2001 |
| WO | WO 02/28366 A2 | 4/2002 |
| WO | WO 02/43800 A2 | 6/2002 |
| WO | WO 02/067895 A2 | 9/2002 |
| WO | WO 03/041684 A2 | 5/2003 |
| WO | WO 03/041684 A3 | 5/2003 |
| WO | WO 03/072133 A1 | 9/2003 |
| WO | WO 04/052336 A2 | 6/2004 |
| WO | WO 2004/089335 A2 | 10/2004 |
| WO | WO 2005/048930 A2 | 6/2005 |

OTHER PUBLICATIONS

International Search Report, dated Aug. 12, 2004 (4 pages).
International Search Report, dated Nov. 12, 2004 (4 pages).
PCT International Search Repoert, dated Jul. 28, 2006 (4 pages).

* cited by examiner

OSMOTIC PUMP WITH MEANS FOR DISSIPATING INTERNAL PRESSURE

CROSS-REFERENCE TO RELATED APPLICATION

Pursuant to the provisions of 35 U.S.C. § 119(e), this application claims the benefit of the filing date of provisional patent application Ser. No. 60/459,296, filed Mar. 31, 2003, for "Osmotic Pump With Means For Dissipating Internal Pressure."

FIELD OF THE INVENTION

The present invention relates to implantable osmotic pumps providing sustained delivery of a drug. In particular, the present invention is directed to an implantable osmotic pump including a vent that allows gradual venting of osmotic material after the drug formulation included in the osmotic pump is delivered.

BACKGROUND

Implantable, controlled-release osmotic pumps (hereinafter "osmotic pumps") are known in the art. For example, U.S. Pat. Nos. 3,797,492, 3,987,790, 4,008,719, 4,865,845, 5,057,318, 5,059,423, 5,112,614, 5,137,727, 5,151,093, 5,234,692, 5,234,693, 5,279,608, 5,336,057, 5,728,396, 5,985,305, 5,997,527, 5,997,902, 6,113,938, 6,132,420, 6,217,906, 6,261,584, 6,270,787, and 6,375,978, which are assigned to ALZA Corporation of Mountain View, Calif., and are herein incorporated in their entirety by reference, describe various osmotic pumps. The osmotic pumps described in these references may be designed for implantation in a subject of choice and may be configured to deliver a range of drugs at various rates over predetermined periods of time.

Osmotic pumps typically include a reservoir for containing an amount of drug formulation, an osmotic composition, a semipermeable membrane, a delivery orifice, and a piston separating the drug formulation from the osmotic composition. Upon administration to an environment of operation, water is drawn through the semipermeable membrane of the osmotic pump into the osmotic composition, causing the osmotic composition to swell. As the osmotic composition swells, the piston included in the osmotic pump is driven through its stroke, resulting in the expulsion of the drug formulation at a controlled rate through the delivery orifice. The rate of drug release from an osmotic pump may be adjusted by altering the composition or amount of the drug formulation or the osmotic composition included in the osmotic pump. Alternatively, the release rate of drug formulation provided by an osmotic pump may be adjusted by altering the composition or exposed surface area of the semipermeable membrane. Because they allow the controlled delivery of active agent over periods of weeks, months, or even years, osmotic pumps can advantageously provide long-term dosing of a desired drug without requiring frequent visits to a healthcare provider or repetitive self-medication. Therefore, osmotic pumps can work to provide increased patient compliance, reduced irritation at the site of administration, fewer occupational hazards for healthcare providers, reduced waste hazards, and increased therapeutic efficacy through enhanced dosing control.

As drug formulation is delivered from an osmotic pump, the internal pressure generated by the osmotic composition within the pump generally remains relatively low. However, if an osmotic system is left within an environment of operation after the piston included in the osmotic pump reaches the end of its stroke within the reservoir (e.g., after substantially all the drug formulation has been delivered), the osmotic composition will continue to draw water in from the environment of operation. As water is drawn into the osmotic pump without expulsion of a corresponding amount of drug formulation, the pressure within the system may rise to such an extent that a component of the osmotic pump is compromised or physically separated. Where the semipermeable membrane included in an osmotic pump is held in place through a friction fit, such as is described in, for example, U.S. Pat. Nos. 5,985,305, 5,728,396, and 6,156,331, the semipermeable membrane is one of the components that is most likely to be separated from the osmotic pump if the internal pressure of the osmotic system increases well beyond normal operational pressures.

It would, therefore, be an improvement in the art to provide an osmotic pump that allows the placement of a semipermeable membrane through a friction fit mechanism, yet works to prevent a pressure build-up within the pump that results in the dissociation of pump components, such as the semipermeable membrane. Though not likely to be harmful to a subject, the physical separation of one or more components of an implanted osmotic pump may complicate removal of the device from a subject. Moreover, the physical separation of the semipermeable membrane of an osmotic pump may allow a relatively sudden release of the material forming the osmotic composition, which may result in localized discomfort or inflammation. Thus, where an implantable osmotic pump is designed to dissipate internal pressure before such pressure reaches a level that could cause dissociation of one or more parts, the design of the osmotic pump would ideally allow pressure dissipation without causing a release of osmotic material that results in discomfort or inflammation.

SUMMARY OF THE INVENTION

The present invention is directed to an osmotic pump that includes a means for venting the osmotic composition included therein before the internal pressure of the pump has the opportunity to build to such an extent that the pump is structurally compromised, such as when one or more components of the pump are physically separated. The means for venting osmotic material included in an osmotic pump according to the present invention includes a vent that allows the material included in the osmotic composition of the pump to dissipate into an environment of operation, resulting in a reduction of the internal pressure.

The vent included in an osmotic pump of the present invention is formed through the reservoir of the osmotic pump and is positioned such that the vent is sealed from the osmotic composition under normal operating conditions. However, the vent is also positioned in the reservoir such that, if the pressure within the osmotic pump reaches a magnitude that results in displacement of one or more components, the vent is opened or exposed to the materials forming the osmotic composition, which allows release of materials forming the osmotic composition into the environment of operation and results in the dissipation of the internal pressure before one or more components of the osmotic pump fails or is separated from the device. In addition, because an osmotic pump according to the present invention can be designed without compressive elements, the maximum rate of material expulsion from the vent will typically match the targeted release rate of the osmotic pump. Therefore, an osmotic pump according to the present invention can be easily designed to allow venting of the osmotic composition, while reducing or minimizing the likelihood that such venting will result in discomfort or irritation to the subject.

In a preferred embodiment, an osmotic pump includes a vent that is sealed by the semipermeable membrane of the osmotic pump during normal operating conditions. The semipermeable membrane of such an embodiment is friction fit within the reservoir and is designed to allow progressive displacement of the semipermeable membrane once a threshold pressure is reached within the osmotic pump. The vent included in this embodiment of the present invention is positioned such that, if the internal pressure reaches the threshold pressure and the semipermeable membrane begins to be displaced relative to the reservoir, the vent is exposed well before the semipermeable membrane is separated from the device. Once the vent is exposed, the osmotic materials included in the osmotic composition may be expelled from the osmotic pump, resulting in a decrease in pressure within the pump and preventing separation of the semipermeable membrane.

BRIEF DESCRIPTION OF THE DRAWINGS

The present invention is described with reference to the accompanying drawings in which like elements bear like reference numerals, and wherein.

DETAILED DESCRIPTION OF THE INVENTION

Figure 1:
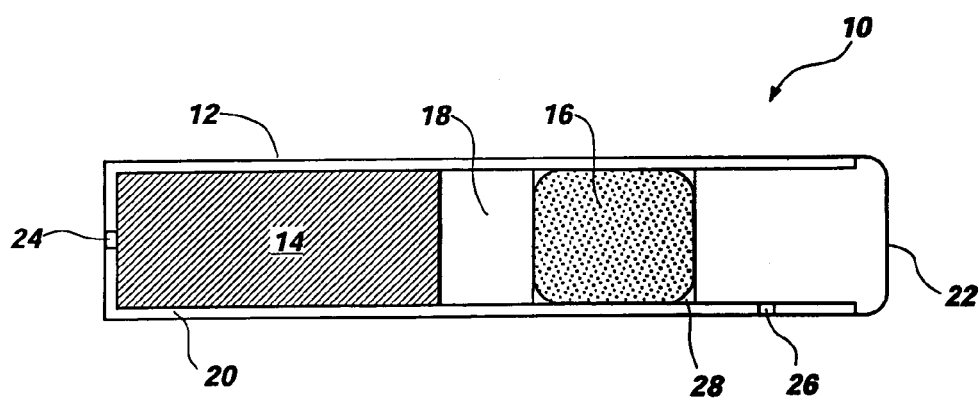
FIG. 1 provides a schematic illustration of one embodiment of an osmotic pump according to the present invention.

An osmotic pump 10 according to the present invention is illustrated in FIG. 1. As can be seen by reference to these figures, an osmotic pump 10 according to the present invention includes a reservoir 12, a drug formulation 14, an osmotic composition 16, a piston 18, a semipermeable membrane 22, a delivery orifice 24, and a vent 26 formed through the wall 20 of the reservoir 12. However, the configuration of the osmotic pump 10 illustrated in FIG. 1 provides only one example of an osmotic pump according to the present invention and is not to be construed as limiting the present invention. The present invention is generally applicable to osmotic pumps, and an osmotic pump according to the present invention may be designed to conform to a wide range of desired sizes or shapes. Moreover, an osmotic pump according to the present invention may be designed for application in various environments or administration by various routes, such as by oral administration, ruminal administration, or implantation.

The reservoir 12 of the osmotic pump 10 of the present invention may be sized and shaped as desired to suit a desired application or to facilitate placement of the osmotic pump 10 in a desired environment of operation. Materials suitable for forming the reservoir 12 must be sufficiently strong to ensure that the reservoir 12 does not leak, crack, break, or significantly distort under stresses to which it is subjected to during administration and operation of the osmotic pump 10. In particular, the reservoir 12 is formed of a material that is sufficiently rigid to withstand expansion of the osmotic composition 16 without undergoing substantial changes to the size or shape of the reservoir 12. The material used to form the reservoir 12 is also chosen to be largely impermeable to fluids from the environment of operation and to the material constituents included in the drug formulation 14 and the osmotic composition 16. As it is used herein the term "largely impermeable" indicates that the migration of materials into or out of the osmotic pump through the material forming the reservoir 12 is so low that any such migration of materials has substantially no adverse impact on the function of the device.

The material used to form the reservoir 12 of an osmotic pump 10 according to the present invention is preferably not a bioerodible material and will remain intact even after the drug formulation 14 has been delivered. Such a design facilitates recovery or passage of the osmotic pump 10 after the drug formulation 14 contained therein has been delivered to a subject. Typical materials suitable for the construction of the reservoir 12 of an osmotic pump 10 according to the present invention include, but are not limited to, nonreactive polymers and biocompatible metals and alloys. Specific examples of suitable polymers include, but are not limited to, polyimide, polysulfone, polycarbonate, polyethylene, polypropylene, polyvinylchloride-acrylic copolymer, polycarbonate-acrylonitrile-butadiene-styrene, polystyrene, acrylonitrile polymers, such as acrylonitrile-butadiene-styrene terpolymer and the like, halogenated polymers, such as polytetrafluoroethylene, polychlorotrifluorethylene copolymer, tetrafluorethylene and hexafluoropropylene. Metallic materials useful in forming the reservoir 12 include, but are not limited to, stainless steel, titanium, platinum, tantalum, gold, and their alloys, as well as gold-plated ferrous alloys, platinum-plated ferrous alloys, cobalt-chromium alloys, and titanium nitride coated stainless steel.

The semipermeable membrane 22 included in an osmotic pump 10 of the present invention is formulated and prepared to be permeable to the passage of external liquids, such as water and biological liquids, but substantially impermeable to the passage of the drug, osmopolymers, osmagents, and the like that may be included in the osmotic pump 10. Suitable materials and methods for forming the semipermeable membrane 22 included in an osmotic pump 10 of the present invention are well known in the art and are detailed in, for example, U.S. Pat. Nos. 3,797,492, 3,987,790, 4,008,719, 4,865,845, 4,874,388, 5,057,318, 5,059,423, 5,112,614, 5,137,727, 5,151,093, 5,234,692, 5,234,693, 5,279,608, 5,336,057, 5,728,396, 5,985,305, 5,997,527, 5,997,902, 6,113,938, 6,132,420, 6,217,906, 6,261,584, 6,270,787, and 6,375,978, the contents of which are herein incorporated in their entirety by this reference. Such possible semipermeable materials from which the semipermeable membrane 22 can be made include, but are not limited to, for example, Hytrel polyester elastomers (DuPont), cellulose esters, cellulose ethers, and cellulose ester-ethers, water flux enhanced ethylene-vinyl acetate copolymers, semipermeable membranes made by blending a rigid polymer with water-soluble low molecular weight compounds, and other semipermeable materials well known in the art. The above cellulosic polymers have a degree of substitution, D.S., on the anhydroglucose unit, from greater than 0 up to 3 inclusive. By "degree of substitution," or "D.S.," is meant the average number of hydroxyl groups originally present on the anhydroglucose unit comprising the cellulose polymer that is replaced by a substituting group. Representative materials include, but are not limited to, one selected from the group consisting of cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53%, and a hydroxyl content of 0.5% to 4.7%; cellulose acetate butyrate having a D.S. of 1.8, an acetyl content of 4% average weight percent, and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose, such as cellulose acetate butyrate and cellulose, cellulose acetate propionate, and the like. Other materials that may be used to prepare a semipermeable membrane 22 useful in the osmotic pump 10 of the present invention include polyurethane, polyetherblockamide (PEBAX, commercially available from ELF ATOCHEM, Inc.), and injection-moldable thermoplastic polymers with some hydrophilicity such as ethylene vinyl alcohol (EVA).

The osmotic composition 16 included in the osmotic pump 10 of the present invention may be formed of any material that creates sufficient osmotic pressure to draw water into the osmotic composition 16 through the semipermeable membrane 22 such that the osmotic composition 16 causes delivery of the drug formulation 14 at a desired rate over a preselected period of time. Preferably, the osmotic composition 16 is formed as one or more osmotic tablets formed of an initially solid or nonflowable composition. However, the osmotic composition 16 included in an osmotic pump 10 according to the present invention is not limited to a tableted and initially solid or nonflowable composition. The osmotic composition 16 loaded into a reservoir 12 of an osmotic pump 10 according to the present invention may be formed in any suitable shape, texture, density, and consistency. For example, instead of a solid, tableted composition, it is possible that the osmotic composition 16 may be loaded into the reservoir 12 as a powdered material.

The osmotic composition 16 includes an osmotic agent. The osmotic agent included in the osmotic composition is a water-attracting agent that serves to draw water into the osmotic pump 10 through the semipermeable membrane 22 and drive the flow of drug formulation 14 out from the osmotic pump 10. The osmotic agent included in the osmotic composition 16 may be an osmagent, an osmopolymer, or a mixture of the two. Methods and formulations for providing osmotic compositions that are suitable for use in an osmotic pump according to the present invention are well known. For example, the patent references that are cited and incorporated by reference herein detail methods and materials suitable for forming osmotic compositions that may be used in an osmotic pump 10 according to the present invention.

Materials that fall within the category of osmagent include materials that are nonvolatile, soluble in water, and create an osmotic gradient suitable for driving the influx of water into the osmotic pump 10. Examples of osmagents that may be useful in the osmotic composition 16 of an osmotic pump 10 of the present invention include, but are not limited to, magnesium sulfate, magnesium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides, and polysaccharides, such as sucrose, glucose, lactose, fructose, and dextran, as well as mixtures of any of these various species.

Materials that fall within the category of osmopolymer are hydrophilic polymers that swell upon contact with water. Osmopolymers may be natural (i.e., of plant or animal origin) or synthetic, and examples of osmopolymers are well known in the art. Particular osmopolymers that may be used in the osmotic composition 16 of an osmotic pump 10 of the present invention include, but are not limited to, poly (hydroxy-alkyl methacrylates) with molecular weights of 30,000 to 5,000,000, poly(vinylpyrrolidone) with molecular weights of 10,000 to 360,000, anionic and cationic hydrogels, polyelectrolyte complexes, poly(vinyl alcohol) having low acetate residual, optionally cross linked with glyoxal, formaldehyde or glutaraldehyde and having a degree of polymerization of 200 to 30,000, a mixture of methyl cellulose, cross linked agar and carboxymethylcellulose, a mixture of hydroxypropyl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, Carbopol® acidic carboxy polymers having molecular weights of 80,000 to 200,000, Polyox Polyethylene oxide polymers having molecular weights of 10,000 to 5,000,000, starch graft copolymers, and Aqua-Keeps™ acrylate polymer polysaccharides.

In addition to an osmotic composition 16, an osmotic pump 10 according to the present invention may also include an additive or filler 28 distributed around the osmotic composition 16. This filler 28 may be any flowable composition, such as a liquid or gel composition, which is substantially incompressible, is suitable for use in the intended environment of operation, is compatible with the other components of the osmotic pump, works to displace air or gas from around the osmotic composition 16, and does not cause the osmotic composition 16 to swell and freeze-up, as described in U.S. Pat. No. 6,132,420. Materials and methods suitable for providing a filler 28 suitable for use in an osmotic pump according to the present invention are also described in U.S. Pat. No. 6,132,420, the contents of which are herein incorporated in their entirety by reference.

The use of a filler 28 is particularly helpful where the osmotic composition 16 is formed as a tableted composition. Machining and tableting tolerances require that there be a gap between the osmotic composition 16 and the surrounding reservoir wall 20. Small irregularities in the shape or contour of the tableted material may also create a gap between the osmotic composition 16 and a piston 18 included in an osmotic pump 10 according to the invention. Such gaps, which can typically range from between about 0.001 to 0.1 inches, are filled with air or other gaseous material, and even the smallest of such air gaps can create a start-up delay of several days to weeks. Additionally, air-filled gaps problematically affect the delivery rate of drug formulation when the osmotic pump is subjected to different external pressures, such as when a patient with an implanted osmotic pump scuba dives or travels to higher altitudes. The inclusion of a filler 28 serves to reduce or eliminate the extent to which any gaps around the osmotic composition 16 are filled with air or another gaseous material and, thereby, works to reduce or eliminate the delays and drug delivery inconsistencies that such gaps can produce.

The movable piston 18 included in an osmotic pump 10 according to the present invention is configured to fit within the reservoir 12 in a sealed manner that allows the piston 18 to be displaced within the reservoir 12 as water is taken into the osmotic composition 16 and the osmotic composition 16 expands. In a preferred embodiment, the piston 18 is formed of a substantially noncompressible material. Moreover, a piston 18 suitable for use in an osmotic pump 10 of the present invention is preferably formed of a material that is impermeable to the osmotic composition 16 and the drug formulation 14, and may include one or more protrusions, which work to form a seal between the piston 18 and the wall 20 of the reservoir 12. Materials suitable for use in a piston 18 included in an osmotic pump 10 of the present invention include metallic materials, such as metal alloys, elastomeric materials, such as the nonreactive polymers already mentioned herein, as well as elastomers in general, such as polyurethanes, polyamides, chlorinated rubbers, styrene-butadiene rubbers, and chloroprene rubbers.

As can be seen by reference to FIG. 1, the delivery orifice 24 included in an osmotic pump 10 of the present invention may simply include an orifice formed through one end of the wall 20 of the reservoir 12. Such a delivery orifice 24 can be provided using, for example, known molding methods or known mechanical or laser drilling methods. If desired, the reservoir 12 of an osmotic pump 10 of the present invention may include more than one delivery orifice 24. In an alternative embodiment, the delivery orifice 24 of an osmotic pump 10 of the present invention may be formed by an outlet plug (not illustrated) that is positioned at least partially within the reservoir 12. Such an outlet plug may be configured, for example, to provide a delivery orifice 24 that optimizes flow of drug formulation 14 or to regulate back diffusion of environmental fluids into the osmotic pump 10. Where the delivery orifice 24 of the osmotic pump 10 of the present invention is formed by an outlet plug, however, the outlet plug is prepared from a substantially noncompressible material. Outlet plugs suitable for application in an osmotic pump according to the present invention are known in the art and are described in, for example, U.S. Pat. Nos. 5,985,305, 6,217,906, and 5,997,527, the contents of each of which are herein incorporated in their entirety by reference. The dimensions of the delivery orifice 24, in terms of both diameter and length, will vary depending on, among other factors, the type of drug delivered, the rate at which the drug formulation 14 is expelled from the osmotic pump 10, and the environment into which it is to be delivered.

Although osmotic pumps according to the present invention are preferably designed for and administered to human or animal physiological environments, osmotic pumps according to the present invention are generally applicable for the delivery of beneficial agents to an environment of operation and are not limited in utility to physiological environments. For example, the osmotic pumps according to the present invention may be used in intravenous systems (e.g., attached to an IV pump, and IV bag, or an IV bottle) for delivering beneficial agents to animals or humans, systems for blood oxygenation, kidney dialysis or electrophoresis, systems for delivering, for instance, nutrients or growth regulating compounds to cell cultures, as well as in pools, tanks, reservoirs and the like. Therefore, the osmotic pump 10 of the present invention is applicable to the delivery of beneficial agents in general, and the term "drug" as it is used herein refers to any beneficial agent that may be delivered to an environment of operation and includes, but is not limited to, medicaments, vitamins, nutrients, biocides, sterilization agents, food supplements, sex sterilants, fertility inhibitors, and fertility promoters. Specific drugs that may be delivered by osmotic pumps of the present invention are detailed, for example, in U.S. Pat. No. 6,132,420, the contents of which are incorporated herein by this reference. Additional examples of drugs that may be delivered by an osmotic pump 10 according to the present invention can be found in the other patent references that are cited and incorporated by reference herein.

The drug included in the drug formulation 14 contained within an osmotic pump 10 of the present invention can be present in a wide variety of chemical and physical forms. At the molecular level, the drug may be present as an uncharged molecule, molecular complex, or pharmaceutically acceptable acid addition or base addition salts, such as hydrochlorides, hydrobromides, sulfate, laurylate, oleate, and salicylate. Salts of metals, amines or organic cations may be used for acidic drug compounds. Derivatives of drugs, such as esters, ethers, and amides can also be used. Moreover, the drug formulation 14 included in an osmotic pump 10 according to the present invention may include more than one drug, resulting in an osmotic pump 10 capable of delivering multiple drugs during its functional lifetime.

The drug formulation 14 included in an osmotic pump 10 according to the present invention may include any formulation suitable for delivering a drug from an osmotic pump 10 according to the present invention. The drug formulation 14 may be formulated as any flowable composition, such as a slurry, a suspension, or a solution, capable of delivering the desired drug to a chosen environment of operation. As desired, the drug formulation 14 included in an osmotic pump 10 according to the present invention may include one or more of various ingredients that work to allow delivery of the drug to the desired environment of operation. In particular, the drug formulation 14 included in an osmotic pump according to the present invention may optionally include preservatives, such as one or more antioxidants or other stabilizing agent, permeation enhancers, or carrier materials that are application appropriate. For example, if the osmotic pump is designed for implantation to a human or animal subject, any carrier, preservative, or permeation enhancer used would be a pharmaceutically acceptable material.

As can be seen by reference to FIG. 1, the vent 26 included in an osmotic pump 10 according to the present invention is formed through the wall 20 of the reservoir 12. The vent 26 may be formed by any suitable method, such as by mechanical drilling, laser drilling, molding, or any other known method that may be used to provide a vent 26 of a desired size and shape through the material forming the reservoir 12. The vent 26 is positioned in the reservoir 12 of an osmotic pump according to the present invention such that, during normal operation, it is sealed from the osmotic composition 16 under normal operating conditions. However, the vent 26 is also positioned in the reservoir 12 such that, if the pressure within the osmotic pump 10 reaches a magnitude that causes displacement of one or more components, the vent 26 is opened or exposed, allowing the internal pressure of the osmotic pump 10 to dissipate before one or more components are separated from the osmotic pump 10.

An osmotic pump 10 according to the present invention preferably includes a vent 26 that is initially sealed by the semipermeable membrane 22. In such an embodiment, the semipermeable membrane 22 is friction fit within the reservoir 12 and both the reservoir 12 and the semipermeable membrane 22 are configured such that, as a threshold pressure is reached within the osmotic pump 10, the semipermeable membrane 22 is progressively displaced from within the reservoir 12. As it is used herein, the term "threshold pressure" indicates an internal pressure or range of pressures that will cause the semipermeable membrane 22 included in the osmotic pump 10 to begin to be displaced within the reservoir 12, but will not result in immediate separation of the semipermeable membrane 22 from the osmotic pump 10. The materials and configuration of both the semipermeable membrane 22 and the reservoir 12 may be altered, as desired, to achieve a semipermeable membrane that is progressively displaced at different threshold pressures. For instance, the semipermeable membrane 22 may be configured as a plug with multiple retaining rings (not shown) that function to increase the threshold pressure of the semipermeable membrane and work to facilitate progressive expulsion once the threshold pressure is reached.

The position of the vent 26 in the reservoir 12 is chosen to provide a vent 26 that is effectively sealed by the semipermeable membrane 22 during normal operation of the osmotic pump 10. However, the vent 26 is also positioned to ensure the vent 26 is opened if the internal pressure of the osmotic pump 10 reaches or exceeds the threshold pressure for the semipermeable membrane 22. As the vent is opened, the osmotic material included in the osmotic composition 16 is released into the environment of operation, resulting in the dissipation of the internal pressure below the threshold pressure required to displace the semipermeable membrane 22. The positioning of the vent 26 is chosen to ensure venting of the osmotic composition 16 and dissipation of the internal pressure before the semipermeable membrane 22 is displaced to such a degree that the semipermeable membrane 22 could separate from the osmotic pump when subjected to mechanical, chemical, or thermal stresses that are typical of the chosen environment of operation.

Because the rate at which water is imbibed into an osmotic pump 10 according to the present invention depends, at least in part, on the surface area of the semipermeable membrane 22 that is exposed to the environment of operation, the vent 26 included in an osmotic pump 10 of the present invention has the potential to affect release rate performance. Where the osmotic pump 10 according to the present invention is configured such that the vent 26 allows aqueous liquid from the environment of operation to contact the semipermeable membrane 22 during normal operation, the increase in exposed surface area provided by the vent 26 will result in an increase in the rate at which water permeates and flows through the semipermeable membrane 22. As a result, an osmotic pump 10 according to the present invention may exhibit relatively shorter start-up times and relatively faster release rates when compared to an osmotic pump that does not include a vent 26 or an osmotic pump that includes a vent that is protected from the environment of operation. Nevertheless, the liquid permeation rate and release rate performance of an osmotic pump 10 according to the present invention can be preselected and controlled through, for example, selection or alteration of the materials used to form the semipermeable membrane, the geometry of the semipermeable membrane, and the surface area and location of the exposed portions of the semipermeable membrane.

In addition, the potential impact that a vent 26 may have on the permeation or release rate provided by the semipermeable membrane 22 of the osmotic pump 10 of the present invention can be mitigated or avoided altogether. For example, as the size of the vent 26 included in an osmotic pump 10 according to the present invention decreases, any affect that the vent 26 has on the permeation rate of the semipermeable membrane 22 or the release rate of the osmotic pump 10 also decreases. Therefore, in a preferred embodiment, the vent 26 included in an osmotic pump 10 according to the present invention is sized such that the vent 26 increases the exposed surface area of the semipermeable membrane 22 by less than 1% relative to an identical device that does not include the vent 26. In an alternative embodiment, the vent 26 included in the osmotic pump 10 of the present invention is formed as a generally annular orifice that has a diameter of less than 0.01 inches. To avoid altogether any changes in permeation or release rates that may be caused by the vent 26 included in an osmotic pump 10 of the present invention, the vent 26 may be sealed from the environment of operation by a water impermeable material, such as a wax or an oil, that is readily expelled as the vent 26 is opened and osmotic material is released.

Figure 2:
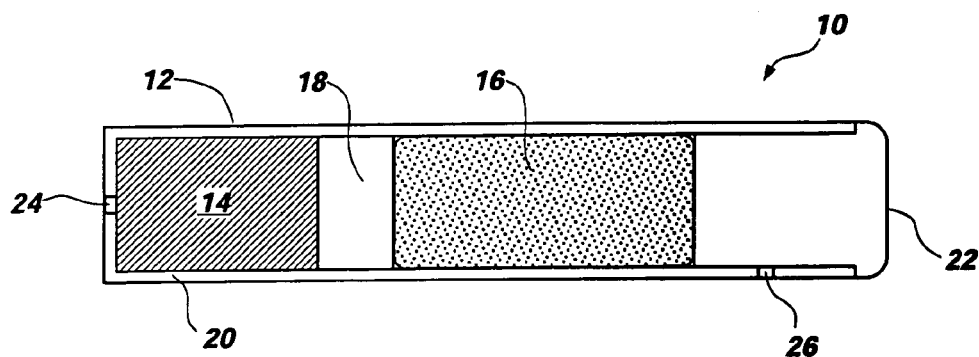
FIG. 2 provides a schematic illustration of the osmotic pump shown in FIG. 1 as the pump functions to deliver drug formulation to an environment of operation.
Figure 3:
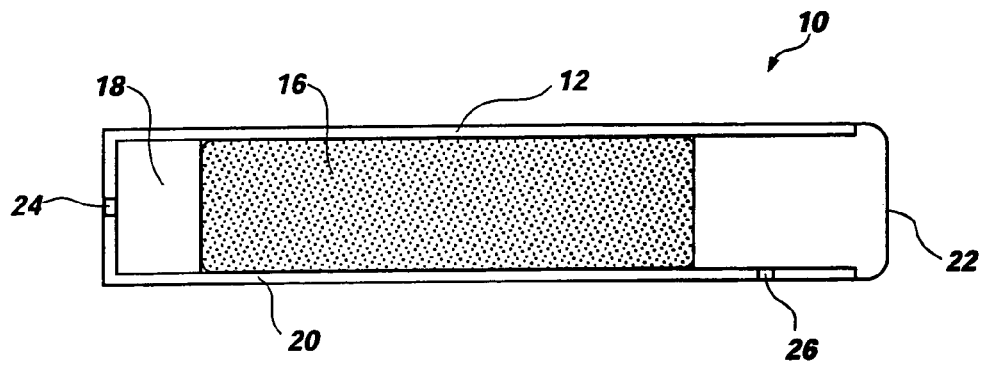
FIG. 3 provides a schematic illustration of the osmotic pump shown in FIG. 1 and FIG. 2 as delivery of the drug formulation is completed and the piston included in the osmotic pump reaches the end of its stroke within the reservoir.
Figure 4:
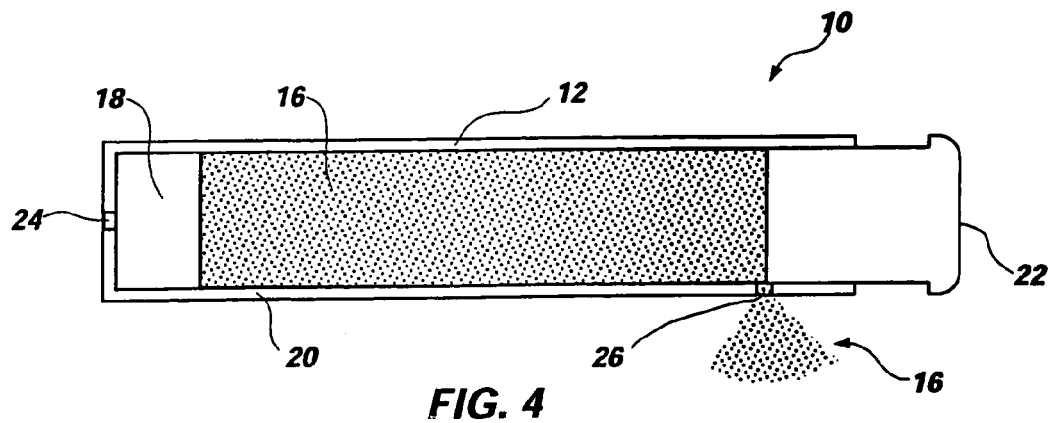
FIG. 4 provides a schematic illustration of the osmotic pump shown in FIG. 1 through FIG. 3 after the internal pressure of the osmotic pump has caused displacement of the semipermeable membrane, the vent has been exposed, and the osmotic composition is venting into the environment of operation.

FIG. 2 through FIG. 4 illustrate the general function of an osmotic pump 10 according to the present invention. Once an osmotic pump 10 of the present invention is placed in an environment of operation, aqueous fluid is imbibed through the semipermeable membrane 22 at a predetermined rate into the osmotic composition 16. As can be seen in FIG. 2, as osmotic composition 16 takes up water, the osmotic composition 16 expands and acts against the piston 18, driving the piston 18 through its stroke within the reservoir 12. As the piston 18 is driven through its stroke, the drug formulation 14 is expelled from the osmotic pump 10 at a controlled rate through the delivery orifice 24. Typically, the drug formulation 14 is released from the osmotic pump 10 at a rate equal to the rate at which water is imbibed into the system, and, as a result, the pressure within the osmotic pump 10 remains relatively low as the osmotic pump 10 operates to deliver drug formulation 14 at a controlled rate over time.

After the piston 18 reaches the end of its stroke within the reservoir 12 and the drug formulation has been delivered from the osmotic pump 10 (shown in FIG. 3), water will continue to be taken up through the semipermeable membrane 22. As water continues to be taken into the osmotic composition 16, the internal pressure of the osmotic pump 10 will continue to build, until the threshold pressure for the semipermeable membrane 22 is reached. As is shown in FIG. 4, once the threshold pressure is reached, the semipermeable membrane 22 is displaced and the vent 26 is opened or exposed such that the osmotic material included in the osmotic composition 16 is released through the vent 26 and into the environment of operation. As osmotic materials are released through the vent 26, the internal pressure of the osmotic pump 10 decreases below the threshold pressure, and the displacement of the semipermeable membrane ceases.

The design of the osmotic pump 10 of the present invention not only works to allow venting of the osmotic composition and dissipation of internal pressure, but the design of osmotic pump 10 of the present invention allows such performance to be achieved without causing a release of osmotic material that would result in discomfort or irritation to the subject. In particular, the components of the osmotic pump 10 are designed to be substantially incompressible. As a result, when the pressure within the osmotic pump 10 builds to the extent that the vent 26 is opened, there is no decompression that may otherwise result in the immediate release of an amount of osmotic material that could result in localized irritation or discomfort. Instead, where the vent 26 included in the osmotic pump 10 is opened, the osmotic composition 14 will typically be delivered from the osmotic pump 10 at a maximum rate that is equal to the maximum release rate provided by the osmotic pump 10. Moreover, as the osmotic composition 14 is released through the vent 26, the osmotic composition 14 becomes more dilute and a smaller osmotic gradient is produced across the semipermeable membrane 22, resulting in an exponential decrease in the mass of osmotic material released over time. Therefore, in each of its embodiments, the osmotic pump 10 of the present invention not only works to dissipate internal pressure before it becomes undesirably high, but the design of the osmotic pump 10 allows such dissipation to occur in a way that reduces the risk of discomfort to the subject.

What is claimed is:

1. An osmotic pump for providing sustained delivery of a beneficial agent, comprising:
   a reservoir for holding the beneficial agent and an osmotic agent;
   at least one wall defining a boundary of the reservoir;
   at least one vent formed through the at least one wall; and
   a semipermeable membrane positioned to seal the at least one vent, the semipermeable membrane being capable of displacement relative to the reservoir when a threshold pressure in the osmotic pump is reached, wherein the at least one vent is exposed to the osmotic agent and at least a portion of the osmotic agent is released from the reservoir when the semipermeable membrane is displaced relative to the reservoir.

2. The osmotic pump of claim 1, wherein the at least one vent is sized to increase an exposed surface area of the semipermeable membrane by less than 1%.

3. The osmotic pump of claim 1, wherein the at least one vent comprises an annular orifice having a diameter of less than 0.01 inches.

4. The osmotic pump of claim 1, wherein the at least one vent is sealed from an environment of operation by a water impermeable material that is readily expelled as the at least one vent is exposed to the osmotic agent.

5. The osmotic pump of claim 4, wherein the water impermeable material comprises a wax or an oil.

6. The osmotic pump of claim 1, wherein the semipermeable membrane is friction fit within the reservoir.

7. The osmotic pump of claim 1, wherein the semipermeable membrane is configured for progressive displacement relative to the reservoir when a threshold pressure in the osmotic pump is reached.

8. The osmotic pump of claim 1, wherein the semipermeable membrane is configured as a plug with multiple retaining rings.

9. The osmotic pump of claim 1, wherein the reservoir is made of a non-bioerodible material.

10. The osmotic pump of claim 1, wherein the osmotic agent comprises an osmotic tablet.

11. The osmotic pump of claim 1, wherein the osmotic agent comprises an osmagent, an osmopolymer, or mixtures thereof.

12. The osmotic pump of claim 1, further comprising a filler distributed within the reservoir and around the osmotic agent.

13. The osmotic pump of claim 1, further comprising a movable piston located in the reservoir and between the beneficial agent and the osmotic agent.

14. The osmotic pump of claim 13, wherein the movable piston is formed of a noncompressible material.

15. The osmotic pump of claim 1, wherein the beneficial agent is selected from the group consisting of medicaments, vitamins, nutrients, biocides, sterilization agents, food supplements, sex sterilants, fertility inhibitors, fertility promoters, and combinations thereof.

16. The osmotic pump of claim 1, wherein the beneficial agent is formulated as a slurry, a suspension, or a solution.

17. An implantable osmotic pump for providing sustained delivery of a beneficial agent, comprising:
   a reservoir for holding the beneficial agent and an osmotic agent;
   a semipermeable membrane formulated to be permeable to passage of external liquids and being capable of displacement relative to the reservoir when a threshold pressure in the osmotic pump is reached; and
   a means for venting the osmotic agent out of the reservoir upon displacement of the semipermeable membrane.

18. The implantable osmotic pump of claim 17, wherein the means for venting the osmotic agent comprises a vent formed through a wall that defines a boundary of the reservoir.

19. The implantable osmotic pump of claim 17, wherein the means for venting the osmotic agent comprises a plurality of vents formed through one or more walls that define boundaries of the reservoir.

20. An osmotic pump for providing sustained delivery of a beneficial agent, comprising:
   a reservoir for holding the beneficial agent and an osmotic agent;
   at least one wall defining a boundary of the reservoir;
   at least one vent formed through the at least one wall; and
   a means for removably sealing the at least one vent, the sealing means being capable of displacement relative to the reservoir when a threshold pressure in the osmotic pump is reached to expose the osmotic agent and release at least a portion of the osmotic agent from the reservoir.

21. The osmotic pump of claim 20, wherein the sealing means comprises a semipermeable membrane.

22. The osmotic pump of claim 20, wherein the sealing means comprises a semipermeable membrane that is friction fit within the reservoir.

23. The osmotic pump of claim 20, wherein the sealing means comprises a semipermeable membrane that is configured for progressive displacement relative to the reservoir when a threshold pressure in the osmotic pump is reached.

24. The osmotic pump of claim 20, wherein the sealing means comprises a semipermeable membrane that is configured as a plug with multiple retaining rings.

* * * * *